(12) United States Patent
Pearson et al.

(10) Patent No.: US 6,685,703 B2
(45) Date of Patent: Feb. 3, 2004

(54) GENERATOR AND PROBE ADAPTER

(75) Inventors: Christopher Pearson, Grafton, MA (US); Robert Garabedian, Tyngsboro, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 106 days.

(21) Appl. No.: 10/036,068

(22) Filed: Oct. 19, 2001

(65) Prior Publication Data

US 2003/0078572 A1 Apr. 24, 2003

(51) Int. Cl.[7] .............................................. A61B 18/18
(52) U.S. Cl. ............................. 606/41; 606/42; 606/32
(58) Field of Search ............................ 439/502; 606/41, 606/32, 34, 42

(56) References Cited

U.S. PATENT DOCUMENTS

| | | | | | |
|---|---|---|---|---|---|
| 5,573,424 | A | * | 11/1996 | Poppe | 439/502 |
| 5,833,688 | A | * | 11/1998 | Sieben et al. | 606/41 |
| 6,113,596 | A | * | 9/2000 | Hooven et al. | 606/42 |
| 6,174,309 | B1 | * | 1/2001 | Wrublewski et al. | 606/45 |

* cited by examiner

*Primary Examiner*—Michael Peffley
*Assistant Examiner*—Aaron Roane
(74) *Attorney, Agent, or Firm*—Bingham McCutchen LLP

(57) ABSTRACT

An adapter to couple a dissimilar, normally incompatible radiotherapeutic probe and radio frequency generator includes an adapter body having a proximal connector to be coupled to the generator, a distal connector to be coupled to the dissimilar, normally incompatible radiotherapeutic probe, and one or more electrical elements to emulate one or more operating parameters of a compatible, native radiotherapeutic probe to interface the generator with the dissimilar, normally incompatible radiotherapeutic probe.

14 Claims, 5 Drawing Sheets

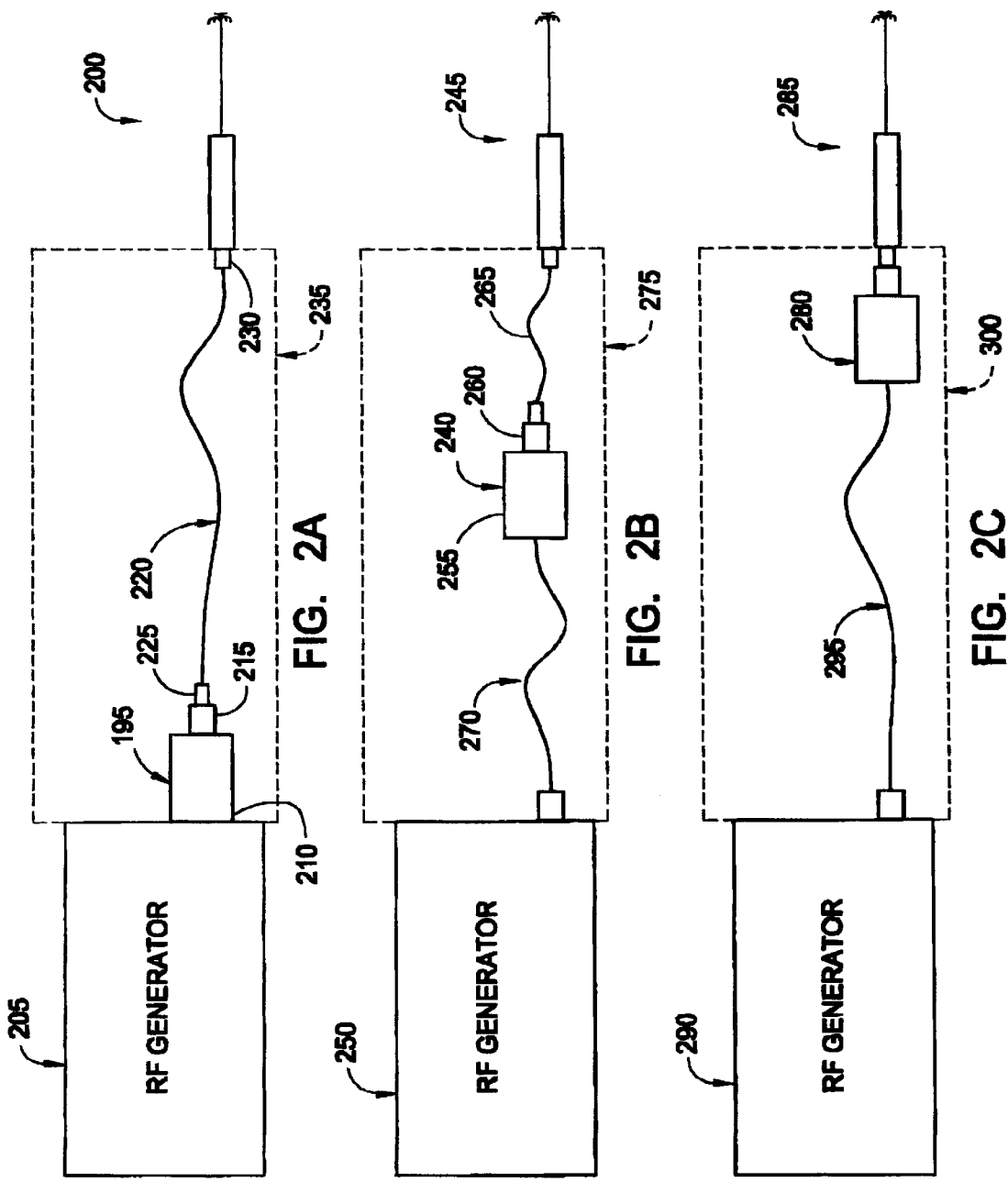

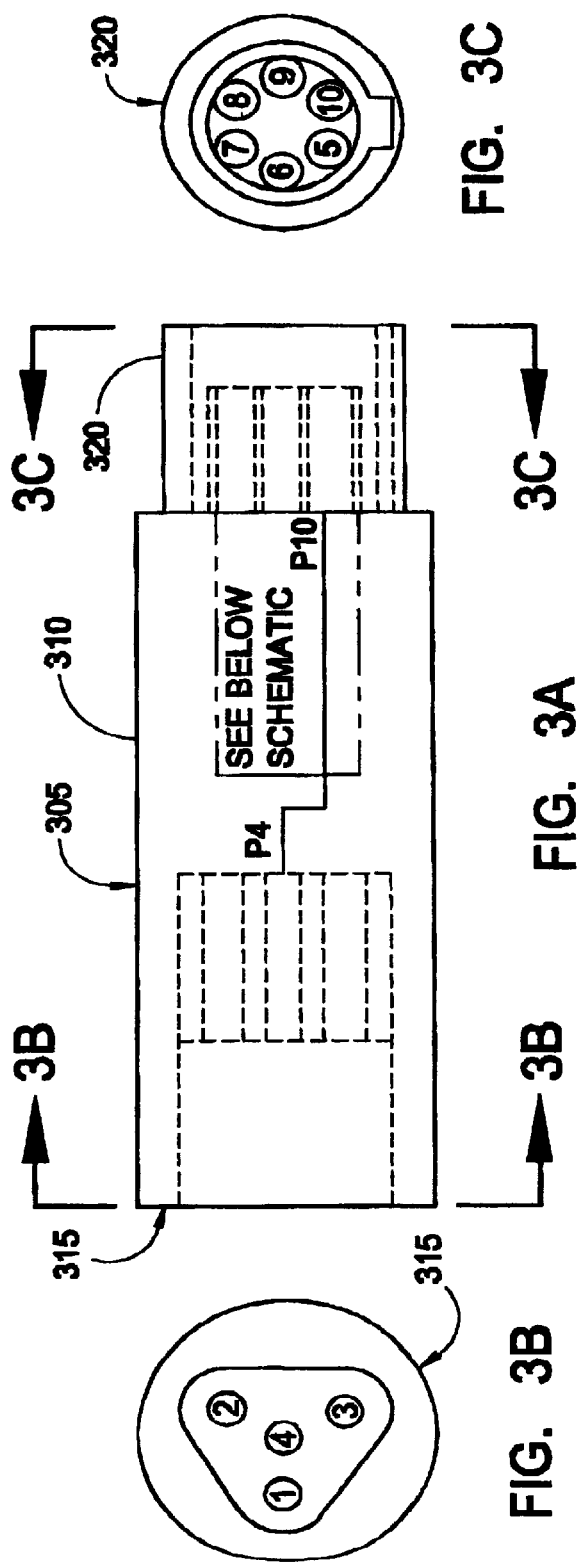
FIG. 3C
FIG. 3A
FIG. 3B
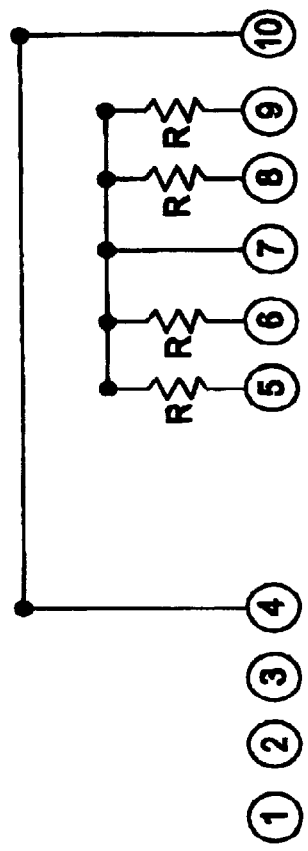
FIG. 3D

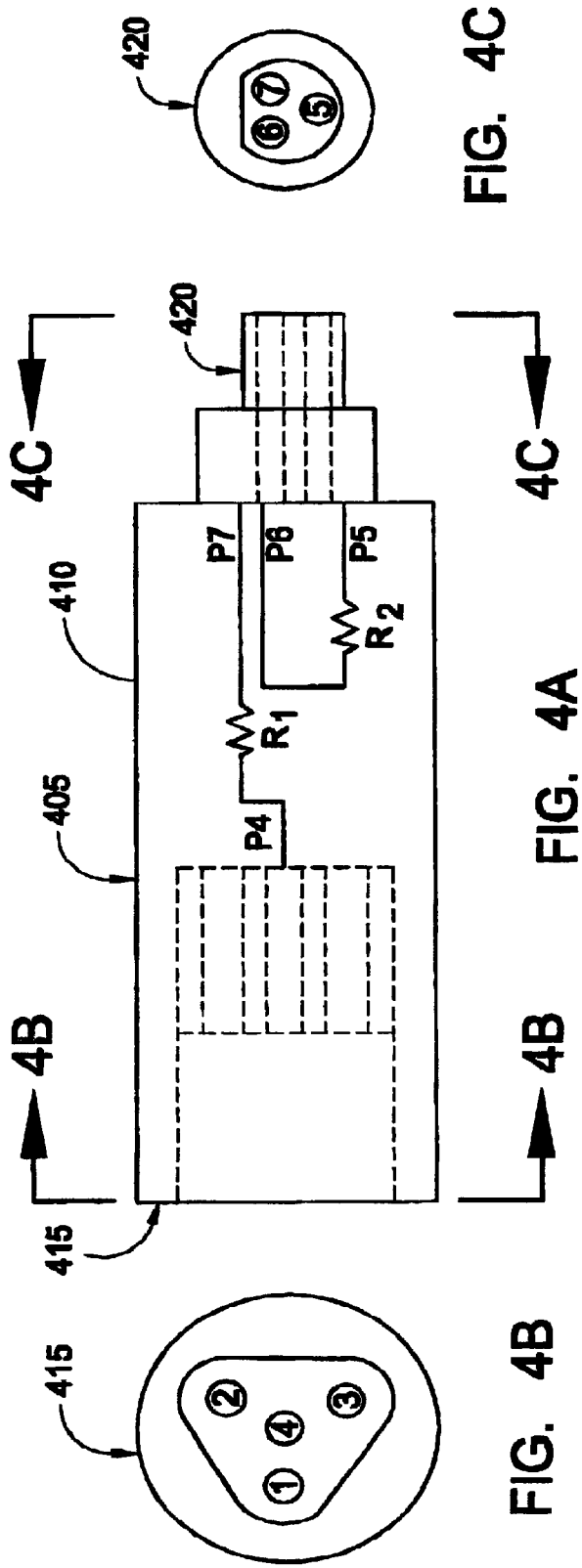
FIG. 4A
FIG. 4B
FIG. 4C
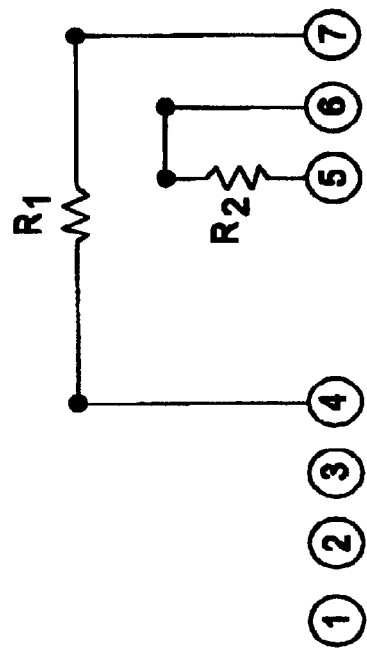
FIG. 4D

GENERATOR AND PROBE ADAPTER

BACKGROUND OF THE INVENTION

1. Field of the Invention

The present invention relates, in general, to adapters for coupling dissimilar, normally incompatible generators and probes, and, in particular, to adapters for coupling dissimilar, normally incompatible radiofrequency generators and probes.

2. Related Art

Physicians in today's health care environment require cost-effective solutions to patient care. For surgeons in particular, the trend favoring minimally invasive procedures aids this requirement through technological advances that make costly procedures and expensive surgery obsolete. For example, medical device manufacturers for many years have harnessed the therapeutic benefits of RF energy in creating devices that deliver minimally invasive localized therapies to patients. Common radiotherapies include tissue incision, coagulation, and ablation, to name just a few. Concentrated RF energy delivered to a targeted tumor or growth in a region of the body may be used to ablate the tumor or growth.

Modern radiotherapy systems are both modular and proprietary. A modular radiotherapy system includes individual system components distributed and sold separately. For instance, a modular radiotherapy system includes a separately sold radio frequency generator and disposable needle electrode probes. Modular means that the system components are interchangeable. A single-use probe may be discarded after use in a procedure and another probe may be attached to the generator for use on the next patient. The proprietary nature of such radiotherapy systems, however, prevents one manufacturer's probe from working with another manufacturer's generator, and vice versa. Thus, hospitals, doctors, and other purchasers making a one-time equipment and/or time investment in a generator lock themselves into a single radiotherapy system manufacturer's solution because only the same manufacturer's probes work with the purchased generator. It should be noted, even if a large capital expenditure is not made in the purchase of a generator (e.g., the generator could be leased in some circumstances), once one or more physicians spend the time to become familiar with a particular manufacturer's generator, it is unlikely that they will switch over to another manufacturer's generator, preventing other manufacturer's probes from being purchased and used.

System incompatibility inhibits industry competition of probe sales because purchasers are locked into only purchasing probes compatible with the generator previously purchased (typically from the same manufacturer as the one that made the generator being used). The inventor of the present invention has recognized that a need exists for an adapter and method to make normally incompatible probes and generators compatible so that purchasers are not forced purchase probes from the same manufacturer as the one that made the generator that is being used.

SUMMARY OF THE INVENTION

An aspect of the invention involves an adapter to couple a dissimilar, normally incompatible radiotherapeutic probe and radio frequency generator. The adapter includes an adapter body having a proximal connector to be coupled to the generator, a distal connector to be coupled to the dissimilar, normally incompatible radiotherapeutic probe, and one or more electrical elements to emulate one or more operating parameters of a compatible, native radiotherapeutic probe to interface the generator with the dissimilar, normally incompatible radiotherapeutic probe.

An additional aspect of the invention involves a kit of adapters to couple a dissimilar, normally incompatible radiotherapeutic probe and a variety of radio frequency generators. The kit includes a variety of different adapters to couple a dissimilar, normally incompatible radiotherapeutic probe and a variety of radio frequency generators. Each adapter includes an adapter body carrying a proximal connector to be coupled to a radio frequency generator, a distal connector to be coupled to the dissimilar, normally incompatible radiotherapeutic probe, and one or more electrical elements to emulate one or more operating parameters of a compatible, native radiotherapeutic probe to interface the generator with the dissimilar, normally incompatible radiotherapeutic probe.

Another aspect of the invention involves a kit to couple a dissimilar, normally incompatible radiotherapeutic probe and a variety of radio frequency generators. The kit includes an adapter having an adapter body carrying a proximal connector to be coupled to a radio frequency generator, a distal connector to be coupled to the dissimilar, normally incompatible radiotherapeutic probe, and one or more electrical elements to emulate one or more operating parameters of a compatible, native radiotherapeutic probe to interface the generator with the dissimilar, normally incompatible radiotherapeutic probe; and one or more connectors to connect the proximal connector of the adapter to one or more of a variety of radio frequency generators.

A further aspect of the invention involves a method of using an adapter to couple a dissimilar, normally incompatible radiotherapeutic probe and radio frequency generator. The method includes providing an adapter having a proximal connector to be coupled to the radio frequency generator, a distal connector to be coupled to the dissimilar, normally incompatible radiotherapeutic probe, and one or more electrical elements to emulate one or more operating parameters of a compatible, native radiotherapeutic probe to interface the generator with the dissimilar, normally incompatible radiotherapeutic probe; coupling the proximal connector to the radio frequency generator; coupling the distal connector to the dissimilar, normally incompatible radiotherapeutic probe; and using the adapter to emulate one or more operating parameters of the compatible, native radiotherapeutic probe to interface the generator with the dissimilar, normally incompatible radiotherapeutic probe.

Further features and advantages of the invention, as well as the structure and operation of various embodiments of the invention, are described in detail below with reference to the accompanying drawings.

BRIEF DESCRIPTION OF THE DRAWINGS

The following drawings illustrate both the design and utility of preferred embodiments of the invention.

FIGS. 2A–2C are block diagrams/schematics illustrating a variety of different embodiments of an adapter to couple a normally incompatible probe and generator.

FIG. 3A is a side-elevational view of an embodiment of an adapter for coupling a normally incompatible probe and generator.

FIG. 3B is an end view of the adapter taken along line 3B—3B in FIG. 3A.

FIG. 3C is an end view of the adapter taken along line 3C—3C in FIG. 3A.

FIG. 3D is an electrical schematic of the pins of the adapter illustrated in FIG. 3A.

FIGS. 4A–4D are similar to FIGS. 3A–3D, but of an alternative embodiment of an adapter for coupling a normally incompatible probe and generator.

DETAILED DESCRIPTION OF THE PREFERRED EMBODIMENTS

Figure 1:
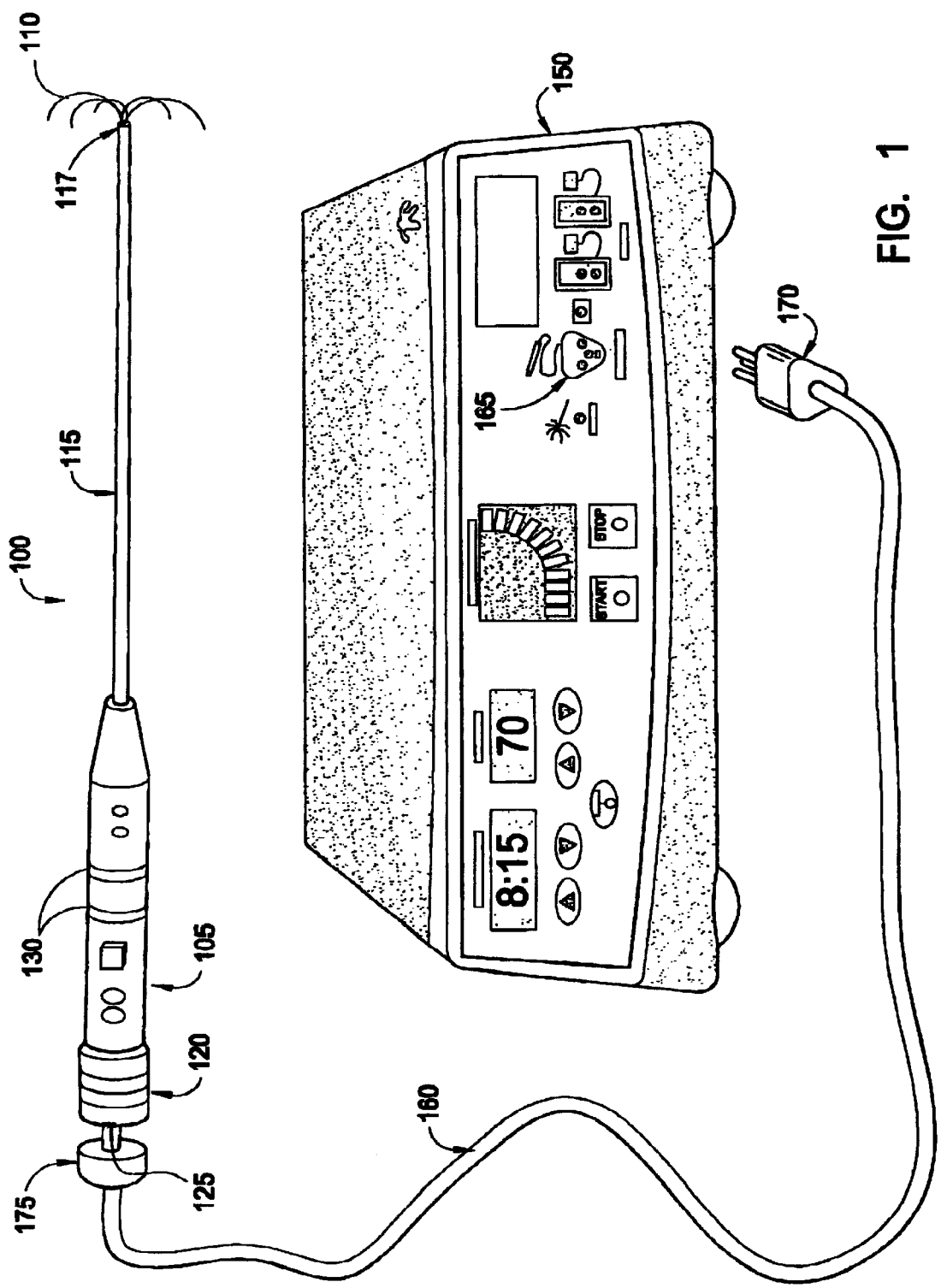
FIG. 1 is a perspective view of an exemplary radiotherapy system including a radiotherapy probe and a RF generator.

With reference to FIG. 1, before describing an embodiment of an adapter for coupling a normally incompatible radiotherapy probe and RF generator, an exemplary radiotherapy system 50 will first be described. The radiotherapy system 50 includes a radiotherapy probe 100 and a RF generator 150.

Although the adapter of the present invention will be described in conjunction with coupling a dissimilar, normally incompatible radiotherapy probe and a RF generator, the adapter may be used to couple other dissimilar, normally incompatible probes and generators. The adapter of the present invention has particular applicability to radiotherapy systems and, in particular, radiotherapy systems for soft tissue ablation and thermal lesion production where RF delivery may be controlled based on impedance, temperature or a combination of both.

The radiotherapy probe 100 includes a handle 105, one or more retractable needle electrodes 110, a trocar 115, a plunger 120, and a port 125. The handle 105 may be made of a light-weight, plastic material and is designed to provide a comfortable grip for a surgeon. The handle 105 may include annular ribs 130 around the circumference of the body 105. The trocar 115 terminates in a sharp distal tip 117 that may be used to pierce body tissue for delivering the distal tip 117 to a targeted ablation site within a patient's body. Once the distal tip is delivered to a targeted ablation site inside the patient's body, the plunger 120 may be engaged to deploy the needle electrodes 110 radially outward, into the body tissue. The electrodes 110 may be made of a metallic material such as Stainless Steel so that when they are deployed they take a distinctive shape such as that shown in FIG. 1.

The RF generator 150 may be used to deliver RF energy to the electrodes 110 through a cable 160. The cable 160 may attach to a port or connector 165 of the generator 150 at one end with a proximal plug or connector 170 and attach to the port 125 of the probe 100 at an opposite end with a distal plug or connector 175. Although the probe 100 may be bipolar, the probe 100 is typically unipolar, meaning the electrodes 110 function electrically as a single electrode in delivering concentrated energy through the tissue region surrounding electrodes 110 to an indifferent electrode on the patient's body.

The proprietary design of the probe 100 and the generator 150 of the radiotherapy system 50 prevents the probe 100 from being used with generators from other manufacturers, i.e., the probe 100 is normally incompatible with generators from other manufacturers. Similarly, a probe made from a manufacturer other than the manufacturer of the generator 150 will not function with the generator 150 because of the thermal, electrical, and/or mechanical incompatibilities between the probe and the generator 150.

With reference to FIG. 2A, an embodiment of an adapter 195 that may be used to couple a dissimilar, normally incompatible probe 200 and generator 205 will be described. The probe 200 may be a probe similar to the probe 100 described above with respect to FIG. 1 and the generator 205 may be a dissimilar, normally incompatible generator made from a different manufacturer than the manufacturer of the probe 200. Alternatively, the generator 205 may be a generator similar to the generator 150 described above with respect to FIG. 1 and the probe 200 may be a dissimilar, normally incompatible probe made from a different manufacturer than the manufacturer of the generator 205.

The adapter 195 includes a proximal connector 210 and a distal connector 215. The proximal connector 210 may be connected directly with an output port or socket on the generator 205 such as the generator output port 165 described above with respect to FIG. 1. A cable 220 such as the cable 160 described above with respect to FIG. 1 may be used to connect the probe 200 to the adapter 195. The cable 220 may be, for example, a straight, coiled, or retractable cord that permits free movement of the probe 200. The cable 160 may terminate at a proximal end in a proximal plug or connector 225 and at a distal end in a distal plug or connector 230. The proximal connector 225 of the cable 220 may connect to the distal connector 215 of the adapter and the distal connector 230 of the cable 220 may connect to an input port or connector of the probe 200 for coupling the probe 200 to the generator 205. Together, the adapter 195 and the cable 220 form an adapter connection system 235 for connecting the probe 200 to the generator 205. In addition to coupling the dissimilar, normally incompatible probe 200 and the generator 205, the adapter 195 is further advantageous in that it allows the same cable 220 that would normally be used with the probe 200 to connect the probe 200 with the adapter 195.

With reference to FIG. 2B, another embodiment of an adapter 240 that may be used to couple a dissimilar, normally incompatible probe 245 and generator 250 will be described. The adapter 240 includes proximal connector 255 and a distal connector 260. A first cable 265 connects the distal connector 260 of the adapter to the probe 245 and a second cable 270 connects the proximal connector 255 to the generator 250. Together, the adapter 240 and the cables 265, 240 form an adapter connection system 275 for connecting the probe 245 to the generator 250. The cables 265, 270 may be separate from the adapter 240, or one or both of the cables 265, 270 may be integral wit the adapter 240. In addition to coupling the dissimilar, normally incompatible probe 245 and the generator 250, the adapter 240 is further advantageous in that it may allow the same cables 265, 270 that would normally be used with the respective dissimilar probe 245 and generator 250 to be used. The adapter connection system 275 may allow a single, universal adapter 240 to be used to couple a variety of different probes 245 and generators 250 because neither the proximal connector 255 nor the distal connector 260 is directly connecting to a connector of the generator 250 or a connector of the probe 245, allowing the connectors 255, 260 to be generic in design.

With reference to FIG. 2C, a further embodiment of an adapter 280 for coupling a dissimilar, normally incompatible probe 285 and generator 290 will be described. The adapter 280 is similar to the adapter 195 described above with respect to FIG. 2C, but instead of connecting directly with a generator, the adapter 280 connects directly with the probe 285. A cable 295 connects the adapter 280 to the generator 290. Together, the adapter 280 and the cable 295 form an adapter connection system 300 for connecting the probe 285 to the generator 290. In addition to coupling the dissimilar, normally incompatible probe 285 and the generator 290, the adapter 280 is further advantageous in that it allows the same cable 295 that would normally be used with the generator 290 to connect the generator 290 with the adapter 280.

The adapter connection system arrangements described above with respect to FIGS. 2A–2C are just a few of the possible arrangements including an adapter for coupling a probe to a generator. The adapter of the present invention may be used in other connection system arrangements for coupling a dissimilar, normally incompatible probe and generator in addition to those described herein.

Figures 5A, 5B, 5C, 5D:
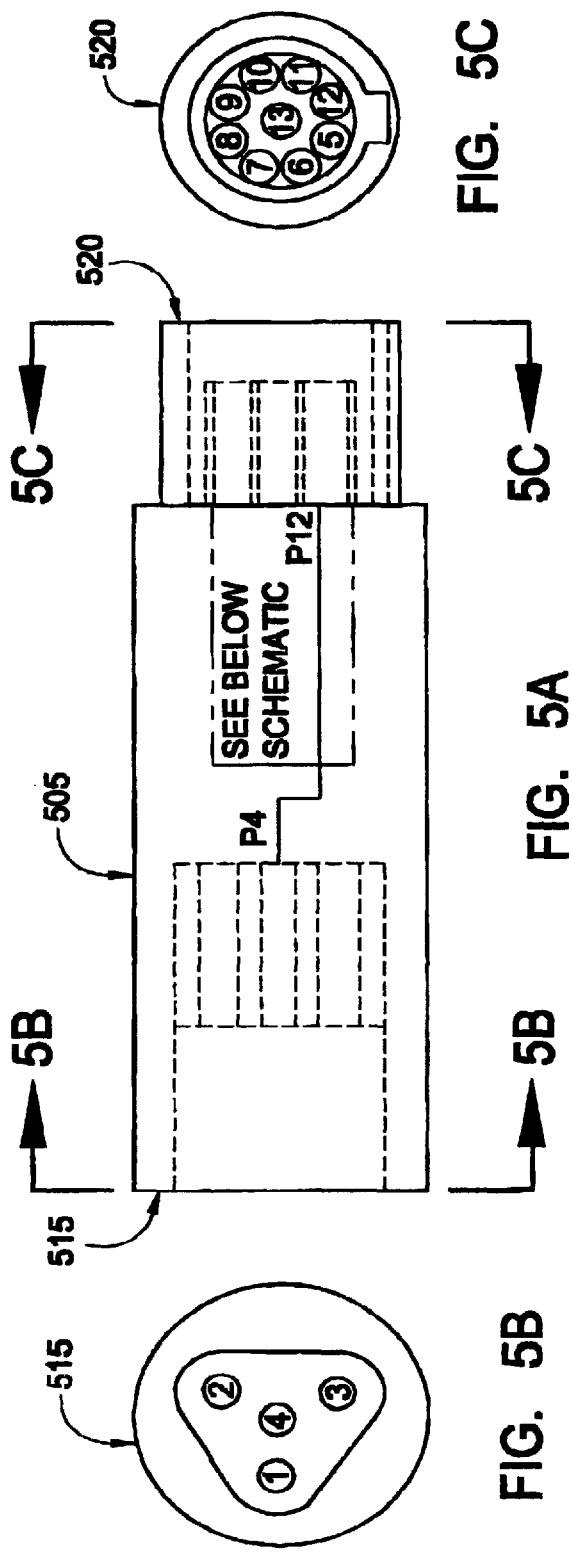
FIGS. 5A–5D are similar to FIGS. 3A–3D, but of another embodiment of an adapter for coupling a normally incompatible probe and generator.

With reference to FIGS. 3–5, a number of different embodiments of an adapter will be described in more detail to show how the adapter allows a dissimilar, normally incompatible probe and generator from two different competing manufacturers to be used together.

With reference to FIGS. 3A–3D, an embodiment of an adapter 305 will be described. It should be noted, the adapter 305 may be used in any of the adapter connection system arrangements described above with respect to FIGS. 2A–2C or other arrangements not described herein. The adapter 305 is designed so that in use the electrical, mechanical, and temperature specifications of the dissimilar, normally incompatible probe and the generator conform so that the generator recognizes the probe and the probe can be used with the generator without uncontrolled dosage or duration of RF energy to body tissue. It is important to prevent impedance and thermal mismatch between the device and the generator. The adapter 305 must be wired in such a way so as to interface the generator with the dissimilar, normally incompatible probe.

The adapter 305 includes an adapter body 310 carrying a distal connector 315 and a proximal connector 320. The distal connector 315 includes a triangular-shaped female receptacle that is coupled to the probe (directly, or via one or ore intermittent connectors, e.g., cable(s)) and includes four pins 1, 2, 3, 4. A center pin 4 is the only active pin and is used for transmission of RF energy from the generator to the probe. Pins 1, 2, and 3 are inactive. The proximal connector 320 includes a round-shaped female receptacle that has a cylindrical stand-off section housing 6 pins centered within and arranged in a circular manner around a central adapter axis. The pins 5, 6, 8, and 9 are connected electrically to temperature measurement thermocouples. Pin 7 is a common ground for the thermocouples. Pin 10 is the active pin used to transmit RF energy to the probe.

In order for the adapter 305 to be compatible with a temperature-driven RF generator, the adapter 305 has to convince the generator that the probe is taking temperature readings. This can be accomplished by placing resistors R at pin locations 5, 6, 8, and 9, and connecting them in parallel to common ground pin 7, as shown in FIG. 3D. The resistors R are selected so that the phantom temperature(s) that they emulate is compatible with the normal operating temperature(s) of a normally used, native probe. The delivery of RF energy to targeted tissue using the adapter 305 and a competitive, normally incompatible probe can be controlled by impedance measurements. Impedance may be measured by application of Ohms law on a current delivered to body tissue via the electrode(s) of the probe and measuring the voltage fluctuation at a return electrode, in a unipolar application, a return electrode externally located on the patient. If the adapter 305 is used with a bipolar electrode arrangement of a probe, impedance may be measured between electrodes on the probe.

With reference to FIGS. 4A–4D, another embodiment of an adapter 405 that may be used in any of the adapter connection system arrangements described above with respect to FIGS. 2A–2C (or other arrangements) will now be described. The adapter 405 is ideally used for coupling a dissimilar probe with an impedance-based generator where the generator is looking for the attached probe to have a certain natural impedance. The adapter 405 includes an adapter body 410 with a distal connector 415 and a proximal connector 420. The distal connector 415 is similar to the distal connector 315 described above with respect to FIGS. 3A–3D. The proximal connector 420 includes a semi-round male connector housing three pins 5, 6, 7. The pins 5, 6 are each connected to a temperature measurement thermocouple. Pin 7 is the active pin used to transmit RF energy.

The adapter 405 may use two resistors R1, R2 to convince the generator that a native, non-competitor probe is being used. The first resistor R1 may be used to increase the impedance of the adapter 405 to match that of the native probe. This is important because the generator used with this embodiment of the adapter 405 utilizes an impedance-based automatic algorithm. Using the first resistor R1 to match the impedance with that of the native probe ensures that the generator and the impedance-based automatic algorithm function seamlessly. A temperature circuit in the native probe is not used interactively by this type of generator, but simply to report temperature. Thus, a second resistor R2 may be used to create a phantom temperature that may be displayed on a front panel of the generator.

With reference to FIGS. 5A–5D, another embodiment of an adapter 505 that may be used in any of the adapter connection system arrangements described above with respect to FIGS. 2A–2C (or other arrangements) will now be described. The adapter 505 is ideally used for coupling a dissimilar probe with a temperature-based or temperature-interactive generator. The adapter 505 includes an adapter body 510 with a distal connector 515 and a proximal connector 520. The distal connector 515 is similar to the distal connector 315 described above with respect to FIGS. 3A–3D. The proximal connector 520 includes a round-shaped female receptacle that has a cylindrical stand-off section housing nine pins 5, 6, 7, 8, 9, 10, 11, 12, 13. The pins 7, 8, 9, 10, 11 are connected electrically to temperature measurement thermocouples. Pin 13 is a common ground pin for the thermocouples. Pin 12 is the active pin used to transmit RF energy. Pins 5 and 6 are inactive.

In order for the adapter 505 to be compatible with the temperature-interactive RF generator 150, the adapter 505 has to convince the generator that the probe is taking temperature readings. This can be accomplished by using resistors R in place of the thermocouples at pin locations 7, 8, 9, 10, 11, and connecting them in parallel to the common ground pin 13. The resistors R are selected so that the phantom temperature that they emulate is compatible with the normal operating temperature of the native probe.

Another aspect of the invention includes a kit of different types of adapters for coupling 1) a variety of different types of probes with one or more types of dissimilar, normally incompatible generators, and/or 2) a variety of different types of generators with one or more types of dissimilar, normally incompatible probes. The kit may include one or more intermittent connectors, e.g., cable(s), that may be required to couple the dissimilar, competitive probe and generator. The adapter(s) may include one or more integral cables or other connectors to couple the dissimilar, normally incompatible probe and generator. Instead of different types of adapters, the kit may include a single type of adapter and one or more different types of connectors for coupling 1) a variety of different types of probes with one or more types of dissimilar, normally incompatible generators, and/or 2) a variety of different types of generators with one or more types of dissimilar, normally incompatible probes.

With the adapter of the present invention, a physician may use probes with a wide variety of generators that before were normally not compatible with a particular probe presently being used. This allows the physician to take advantage of state-of-the-art probe technology or the best probe for the job instead of being locked into only using probes compatible with the current generator being used or having to obtain a new generator.

While embodiments and applications of this invention have been shown and described, it would be apparent to those in the field that many more modifications are possible without departing from the inventive concepts herein. The invention, therefore, is not to be restricted except in the spirit of the appended claims.

What is claimed:

1. A method of using an adapter to couple a dissimilar normally incompatible radiotherapeutic probe and radio frequency generator, the radio frequency generator normally used with a compatible, native radiotherapeutic probe, the method comprising:

providing an adapter including a proximal connector to be coupled to the radio frequency generator, a distal connector to be coupled to the dissimilar, normally incompatible radiotherapeutic probe, and one or more electrical elements to emulate one or more operating parameters of the compatible, native radiotherapeutic probe to interface the generator with the dissimilar, normally incompatible radiotherapeutic probe;

coupling the proximal connector to the radio frequency generator;

coupling the distal connector to the dissimilar, normally incompatible radiotherapeutic probe; and using the adapter to emulate one or more operating parameters of the compatible, native radiotherapeutic probe to interface the generator with the dissimilar, normally incompatible radiotherapeutic probe, wherein the one or more operating parameters of the compatible, native radiotherapeutic probe includes impedance, and the one or more electrical elements include one or more resistors to emulate the impedance of the compatible, native radiotherapeutic probe to interface the generator with the dissimilar, normally incompatible radiotherapeutic probe.

2. The method of claim 1, wherein coupling the proximal connector to the radio frequency generator includes directly connecting the proximal connector to the radio frequency generator.

3. The method of claim 1, wherein coupling the proximal connector to the radio frequency generator includes indirectly connecting the proximal connector to the radio frequency generator via one or more connectors.

4. The method of claim 3, wherein the one or more connectors include a cable.

5. The method of claim 1, wherein coupling the distal connector to the dissimilar, normally incompatible radiotherapeutic probe includes directly connecting the distal connector to the dissimilar, normally incompatible radiotherapeutic probe.

6. The method of claim 1, wherein coupling the distal connector to the dissimilar, normally incompatible radiotherapeutic probe includes indirectly connecting the distal connector to the dissimilar, normally incompatible radiotherapeutic probe via one or more connectors.

7. The method of claim 6, wherein the one or more connectors include a cable.

8. A method of using an adapter to couple a dissimilar normally incompatible radiotherapeutic probe and radio frequency generator, the radio frequency generator normally used with a compatible, native radiotherapeutic probe, the method comprising:

providing an adapter including a proximal connector to be coupled to the radio frequency generator, a distal connector to be coupled to the dissimilar, normally incompatible radiotherapeutic probe, and one or more electrical elements to emulate one or more operating parameters of the compatible, native radiotherapeutic probe to interface the generator with the dissimilar, normally incompatible radiotherapeutic probe;

coupling the proximal connector to the radio frequency generator;

coupling the distal connector to the dissimilar, normally incompatible radiotherapeutic probe; and using the adapter to emulate one or more operating parameters of the compatible, native radiotherapeutic probe to interface the generator with the dissimilar, normally incompatible radiotherapeutic probe, wherein the one or more operating parameters of the compatible, native radiotherapeutic probe includes temperature, and the one or more electrical elements include one or more resistors to emulate the resistance of one or more temperature sensors of the compatible, native radiotherapeutic probe to interface the generator with the dissimilar, normally incompatible radiotherapeutic probe.

9. The method of claim 8, wherein coupling the proximal connector to the radio frequency generator includes directly connecting the proximal connector to the radio frequency generator.

10. The method of claim 8, wherein coupling the proximal connector to the radio frequency generator includes indirectly connecting the proximal connector to the radio frequency generator via one or more connectors.

11. The method of claim 10, wherein the one or more connectors include a cable.

12. The method of claim 8, wherein coupling the distal connector to the dissimilar, normally incompatible radiotherapeutic probe includes directly connecting the distal connector to the dissimilar, normally incompatible radiotherapeutic probe.

13. The method of claim 8, wherein coupling the distal connector to the dissimilar, normally incompatible radiotherapeutic probe includes indirectly connecting the distal connector to the dissimilar, normally incompatible radiotherapeutic probe via one or more connectors.

14. The method of claim 13, wherein the one or more connectors include a cable.

* * * * *